US00PP25515P2

(12) United States Plant Patent
Hanna et al.

(10) Patent No.: US PP25,515 P2
(45) Date of Patent: May 5, 2015

(54) GRASS 'TIFT 10'

(50) Latin Name: ***Pennisetum* hybrid**
Varietal Denomination: Tift 10

(71) Applicant: University of Georgia Research Foundation, Inc., Athens, GA (US)

(72) Inventors: Wayne W. Hanna, Chula, GA (US); S. Kristine Braman, Griffin, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 153 days.

(21) Appl. No.: 13/986,882

(22) Filed: Jun. 13, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Pennisetum* 'Tift 10' is provided. The new and distinct variety has high ornamental value, cold tolerance for short periods of time, and disease resistance. The asexually reproduced variety is reliably propagated vegetatively.

1 Drawing Sheet

Latin name of the genus and species of the plant claimed: 'Tift 10' is a tri-specific ornamental *Pennisetum* hybrid of the genus and species *Pennisetum purpureum*×[*Pennisetum glaucum*×(*Pennisetum purpureum*×*Pennisetum squamulatum*)].

Variety denomination: The new *Pennisetum* claimed is of the variety denominated 'Tift 10'.

BACKGROUND OF THE INVENTION

The present invention relates to a new and distinct cultivar of *Pennisetum* herein referred to as 'Tift 10'.

The new *Pennisetum* 'Tift 10' is a product of a planned breeding program conducted by the Inventors in Tifton, Ga. The objective of the *Pennisetum* breeding program is to create new plant cultivars with improved commercial qualities. This cultivar is commercially important for its superior ornamental value. These and other qualities are enumerated herein.

Pedigree and history: In 2003, red tetraploid (2n=4x=28) pearl millet (unpatented *Pennisetum glaucum*; designated '04-94') was crossed with SC 1125-2 [a Merkeron napiergrass (unpatented *Pennisetum purpureum;* 2n=4x=28) that had been crossed with PS 262 (unpatented *Pennisetum squamulatum;* 2n=8x=56)]. One vigorous plant, from the 04-94/SC 1125-2 cross, designated '04-26-1', was selected in 2004. In 2004, 'Princess' napiergrass (U.S. Plant Pat. No. 17,728; 2n=4x=28, female parent) was pollinated with '04-26-1' (unpatented; male parent). The new variety 'Tift 10' was the tenth plant selected in 2005 from the 2004 cross. The new variety 'Tift 10' has been tested since 2005.

Asexual reproduction of the new *Pennisetum* 'Tift 10' by vegetative propagation (single stem propagules) in a controlled environment in Tifton, Blairsville and Griffin, Ga. since 2005, has shown that the unique features of this new *Pennisetum* hybrid are stable and reproduced true to type in successive generations.

SUMMARY OF THE INVENTION

The following traits have been repeatedly observed and represent the characteristics of a new variety *Pennisetum*, 'Tift 10'. The new variety 'Tift 10' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Tifton, Blairsville, and Griffin, Ga., and are determined to be the unique characteristics of the new variety 'Tift 10':

1. 'Tift 10' reaches a height of about 140 cm and canopy diameter is about 140 cm.
2. 'Tift 10' exhibits a vigorous growth habit.
3. 'Tift 10' is pollen and seed sterile.

The new variety *Pennisetum* 'Tift 10' can be compared to its female parent 'Princess' and its sister hybrid 'Tift-17' (U.S. Plant Pat. No. 21,464).

Plants of the new *Pennisetum* 'Tift 10' differ from its female parent 'Princess' in the following characteristics:

1. The new variety 'Tift 10' is taller than 'Princess'.
2. The new variety 'Tift 10' has a wider canopy diameter, has longer and wider leaves, does not have green mottling in leaves, and is resistant to *Helminthosporium* leaf spot compared to 'Princess'.

Plants of the new *Pennisetum* 'Tift 10' differ from its male parent '04-26-1' in the following characteristics:

1. The new variety 'Tift 10' is slightly different from '04-26-1' in adaxial leaf color. The new variety 'Tift 10' is about Greyed-purple RHS 187A, whereas '04-26-1' is about mottled Greyed-purple RHS 183B/138A.
2. The new variety 'Tift 10' has a different midrib color. The new variety 'Tift 10' has a midrib color that is about Greyed-purple RHS 186B, while '04-26-1' has a midrib color that is about Red-purple RHS 61C.

Plants of the new *Pennisetum* 'Tift 10' differ from its sister hybrid 'Tift-17' in the following characteristics:

1. The new variety 'Tift 10' is significantly taller than 'Tift-17'.
2. Culm-leaf angle is significantly smaller for 'Tift 10' compared to the culm-leaf angle for 'Tift-17'.
3. 'Tift 10' has significantly wider leaves and significantly better color than 'Tift 17'.

The following observations, measurements, and values describe plants grown in Tifton, Blairsville, or Griffin, G. In Tables 1-9, the least significant difference (LSD) is set at P≤0.05 probability level. Growth days were included in ratings. Plants were spaced at 2 meter centers. All data are from plants established as single stem propagules in mid-May and rated in September through October, except the data labeled "Test 1," from 2007 and 2009, in which the plants had been overwintered at Tifton, Ga.

The new variety 'Tift 10' was significantly taller than 'Tift-17' in two of four tests at Tifton, Ga. and in one of two tests at Blairsville, Ga. (Table 1). The canopy diameter and base diameter at ground level were observed to be similar between 'Tift 10' and 'Tift-17' (Tables 2 and 3). Leaf width differences between 'Tift 10' and 'Tift-17' were significant in two of three tests (Table 4). No significant differences were measured between these two cultivars for leaf length (Table 5). Culm-leaf angle was significantly smaller for 'Tift 10' compared to 'Tift-17' (Table 6). 'Tift 10' had significantly more leaves per culm than 'Tift-17' (Table 6). On Dec. 21, 2009 inflorescences were exserted on 'Tift 10' but not on 'Tift-17' (completely vegetative) in three different tests (Table 6). 'Tift 10' produced significantly fewer culms per plant than 'Tift-17' in two of four tests (Table 7). 'Tift 10' had significantly better color than 'Tift-17' in six of six tests (Table 8). *Helminthosporium* leaf spot is known to affect some genotypes in this species but, this disease has not been observed at Tifton, Griffin, or Blairsville, Ga. on 'Tift 10' (Table 9).

TABLE 1

Plant heights (cm) of two ornamental *Pennisetum* grasses planted at three locations in Georgia.

| | Tifton | | | | Blairsville | | Griffin |
|---|---|---|---|---|---|---|---|
| | 2006 | 2007 | 2009 | 2007 | 2006 | 2007 | 2009 |
| Growth days | 158 d Test 1 | 188 d Test 1 | 189 d Test 1 | 151 d Test 2 | 138 d | 123 d | 141 d |
| 'Tift 10' | 125 | 147 | 155 | 108 | 112 | 145 | 154 |
| 'Tift-17' | 115 | 126 | 148 | 99 | 72 | 140 | 137 |
| LSD | NS | 18 | NS | 4 | 31 | NS | NS |

In Table 1, plant heights were measured from ground level to top of plant canopy. All height measurements are in cm. At Tifton, Ga., 'Tift 10' and 'Tift-17' were planted on May 11, 2006, with measurements taken on Sep. 20, 2006, Sep. 17, 2007, and Oct. 6, 2009 ("Test 1"). The plants originally planted in 2006 survived the winters of 2006/2007, 2007/2008, and 2008/2009 in the field. "Test 2" represents a planting of 'Tift 10' and 'Tift-17' that occurred on Apr. 19, 2007, with measurements made on Sep. 17, 2007. At Blairsville, Ga., 'Tift 10' was planted on Jun. 2, 2006 and May 27, 2007, with measurements made on Oct. 18, 2006 and Sep. 27, 2007, respectively. At Griffin, Ga., 'Tift 10' was planted on May 14, 2009 and measurements taken on Oct. 2, 2009.

TABLE 2

Canopy diameter (cm) of individual plant of two ornamental *Pennisetum* grasses planted at three locations in Georgia. Plants were spaced on two meter centers.

| | Tifton | | | Blairsville | | Griffin |
|---|---|---|---|---|---|---|
| | 2006 | 2007 | 2007 | 2006 | 2007 | 2009 |
| Growth days | 158 d Test 1 | 188 d Test 1 | 151 d Test 2 | 138 d | 123 d | 141 d |
| 'Tift 10' | 133 | 143 | 137 | 135 | 155 | 144 |
| 'Tift-17' | 143 | 160 | 133 | 141 | 135 | 163 |
| LSD | NS | NS | 4 | NS | NS | NS |

Plant canopy measurements, as shown in Table 2, represent the average diameters measured at the estimated widest and narrowest portions of a single plant canopy. Measurements are in cm. At Tifton, Ga., 'Tift 10' was planted on May 11, 2006, with measurements taken on Sep. 20, 2006 and Sep. 17, 2007 ("Test 1"). The plants originally planted in 2006 survived the 2006/2007 winter in the field. "Test 2" represents a planting of 'Tift 10' that occurred on Apr. 19, 2007, with measurements made on Sep. 17, 2007. At Blairsville, Ga., 'Tift 10' was planted on Jun. 2, 2006 and May 27, 2007, with measurements made on Oct. 18, 2006 and Sep. 27, 2007, respectively. At Griffin, Ga., 'Tift 10' was planted on May 14, 2009, with measurements taken on Oct. 2, 2009.

TABLE 3

Base diameter (cm) at ground level of individual plants of two ornamental *Pennisetum* grasses planted at two locations in Georgia. Plants were spaced on two meter centers.

| | Tifton | | | Blairsville |
|---|---|---|---|---|
| | 2006 | 2007 | 2007 | 2007 |
| Growth days | 158 d Test 1 | 188 d Test 1 | 151 d Test 2 | 123 d |
| 'Tift 10' | 49 | 40 | 25 | 36 |
| 'Tift-17' | 48 | 44 | 22 | 37 |
| LSD | NS | NS | 3 | NS |

Base diameter is the diameter of the base of a single plant. Measurements are in cm. At Tifton, Ga., 'Tift 10' was planted on May 11, 2006, with measurements taken on Sep. 20, 2006 and Sep. 17, 2007 ("Test 1"). The plants originally planted in 2006 survived the 2006/2007 winter in the field. "Test 2" represents a planting of 'Tift 10' that occurred on Apr. 19, 2007, with measurements made on Sep. 17, 2007. At Blairsville, Ga., 'Tift 10' was planted on May 27, 2007, with measurements made on Sep. 27, 2007.

TABLE 4

Leaf width(mm) of individual plants of two ornamental *Pennisetum* grasses planted at two locations in Georgia. Plants were spaced on two meter centers.

| | Tifton | | Blairsville |
|---|---|---|---|
| | 2006 | 2007 | 2006 |
| Growth days | 158 d Test 1 | 151 d Test 2 | 138 d |
| 'Tift 10' | 42 | 38 | 39 |
| 'Tift-17' | 33 | 30 | 30 |
| LSD | 4 | 2 | NS |

Leaf width measured in the center of the latest fully extended leaf. At Tifton, Ga., 'Tift 10' was planted on May 11, 2006, with measurements taken on Sep. 20, 2006 ("Test 1"). "Test 2" represents a planting of 'Tift 10' that occurred on Apr. 19, 2007, with measurements made on Sep. 17, 2007. At Blairsville, Ga., 'Tift 10' was planted on Jun. 2, 2006, with measurements made on Oct. 18, 2006.

TABLE 5

Leaf length (cm) of individual plants of two ornamental *Pennisetum* grasses planted at two locations in Georgia. Plants were spaced on two meter centers.

| | Tifton | | Blairsville |
|---|---|---|---|
| | 2006 | 2007 | 2006 |
| Growth days | 158 d<br>Test 1 | 151 d<br>Test 2 | 138 d |
| 'Tift 10' | 77 | 61 | 79 |
| 'Tift-17' | 68 | 61 | 83 |
| LSD | NS | NS | NS |

The leaf length was measured from the leaf collar to the leaf tip of the latest fully extended leaf. At Tifton, Ga., 'Tift 10' was planted on May 11, 2006, with measurements taken on Sep. 20, 2006 ("Test 1"). "Test 2" represents a planting of 'Tift 10' and 'Tift-17' that occurred on Apr. 19, 2007, with measurements made on Sep. 17, 2007. At Blairsville, Ga., 'Tift 10' and 'Tift-17' were planted on Jun. 2, 2006, with measurements made on Oct. 18, 2006.

TABLE 6

Leaf angle, leaf number, and heading characteristics of individual plants of two ornamental *Pennisetum* grasses planted at Tifton, Georgia. Plants were spaced on two meter centers.

| | Culm Leaf | Number | Inflorescence Exsertion | | |
|---|---|---|---|---|---|
| Entry | Angle 2008 | Leaves/Culm 2008 | 2006 Test 1 | 2009 Test 2 | 2009 Nursery |
| 'Tift 10' | 19.0 | 11.3 | 3.0 | 2.5 | 2.7 ± 0.5 |
| 'Tift-17' | 27.0 | 9.6 | 1.0 | 1.0 | 1.0 ± 0.0 |
| LSD | 4.5 | 1.3 | 0.2 | 0.5 | — |

The leaf angle and the number of fully extended leaves per culm were measured on plants planted on May 12, 2008, with the measurements occurring on Oct. 10, 2008. The measured leaf angle was the angle observed between the adaxial leaf surface and the culm at the leaf collar on the last fully extended leaf.

The reported inflorescence exsertion data represents the translation of the percentages of culms with fully exserted inflorescences into a numerical score. That is, a score of 1 is assigned to a completely vegetative plant, 2 represents 1-20% of culms with fully exserted inflorescences, 3 (21-30%), 4 (31-40%), 5 (41-50%), 6 (51-60%), 7 (61-70%), 8 (71-80%), and 9 (>80%).

'Tift 10' and 'Tift-17' were planted on May 11, 2006 ("Test 1"). These plants survived the winters of 2006/2007, 2007/2008, and the 2008/2009 at Tifton, Ga. The plants of "Test 2" were planted on May 7, 2009, while the plants termed "Nursery" were planted on May 9, 2009. All ratings were made on Dec. 21, 2009.

TABLE 7

Total number of culms on individual plants of two ornamental *Pennisetum* grasses planted at two locations in Georgia. Plants were spaced on two meter centers.

| | Tifton | | | Blairsville |
|---|---|---|---|---|
| | 2006 | 2007 | 2007 | 2006 |
| Growth days | 158 d<br>Test 1 | 188 d<br>Test 1 | 151 d<br>Test 2 | 138 d |
| 'Tift 10' | 35 | 39 | 24 | 38 |
| 'Tift-17' | 52 | 61 | 27 | 65 |
| LSD | NS | NS | 3 | 16 |

At Tifton, Ga., 'Tift 10' and 'Tift-17' were planted on May 11, 2006, with measurements taken on Sep. 20, 2006 and Sep. 17, 2007 ("Test 1"). The plants originally planted in 2006 survived the winter of 2006/2007 in the field. "Test 2" represents a planting of 'Tift 10' and 'Tift-17' that occurred on Apr. 19, 2007, with measurements made on Sep. 17, 2007. At Blairsville, Ga., 'Tift 10' and 'Tift-17' were planted on Jun. 2, 2006, with measurements taken on Oct. 18, 2006.

TABLE 8

Color ratings of individual plants of two ornamental *Pennisetum* grasses planted at three locations in Georgia. Plants were spaced on two meter centers.

| | Tifton | | | Blairsville | | Griffin |
|---|---|---|---|---|---|---|
| | 2006 | 2009 | 2007 | 2007 | 2009 | 2009 |
| Growth days | 158 d<br>Test 1 | 181 d<br>Test 1 | 151 d<br>Test 2 | 123 d | 163 d | 141 d |
| 'Tift 10' | 8.8 | 9.0 | 7.8 | 8.0 | 9.0 | 9.0 |
| 'Tift-17' | 7.8 | 7.6 | 7.0 | 7.0 | 7.3 | 8.0 |
| LSD | 0.7 | 0.6 | 0.5 | 0.8 | 0.7 | 0.5 |

Color ratings are measured on a scale of 1 to 9, where 1 represents green and 9 represents dark purple/red. At Tifton, Ga., 'Tift 10' and 'Tift-17' were planted May 11, 2006, with measurements taken on Sep. 20, 2006 and Oct. 6, 2009 ("Test 1"). "Test 2" represents a planting of 'Tift 10' and 'Tift-17' that occurred on Apr. 19, 2007, with measurements made on Sep. 17, 2007. Color in Test 2 was rated on young propagules in the greenhouse on Jan. 28, 2007 before the plants were transplanted to the field. At Blairsville, Ga., 'Tift 10' and 'Tift-17' were planted on May 27, 2007 and Apr. 28, 2009, with measurements taken on Sep. 18 and 27, 2007 and Oct. 8, 2009, respectively. At Griffin, Ga., 'Tift 10' and 'Tift-17' were planted on May 14, 2009, with measurements taken Oct. 2, 2009.

TABLE 9

*Helminthosporium* leaf spot ratings on three ornamental *Pennisetum* grasses planted at three locations in Georgia.

| | Tifton | Blairsville | | Griffin |
|---|---|---|---|---|
| | 2008 | 2006 | 2007 | 2009 |
| Growth days | 153 d<br>Oct. 10 | 138 d<br>Oct. 18 | 123 d<br>Oct. 27 | 141 d<br>Oct. 2 |
| 'Tift 10' | 1.0 | 1.0 | 1.0 | 1.0 |
| 'Tift-17' | 1.0 | 1.0 | 1.0 | 1.0 |
| 'Princess' | 5.8 | 3.5 | 3.5 | 6.6 |
| LSD | 0.2 | 0.6 | 0.5 | 0.6 |

Disease ratings in Table 9 are defined as follows: 1=No disease, 2=1-20%, 3=21-30%, 4=31-40%, 5=41-50%, 6=51-60%, 7=61-70%, 8=71-80%, 9=>80% leaves infected. Symptoms occur in the field during late August and September. At Tifton, Ga., 'Tift 10' and 'Tift-17' were planted on May 12, 2008, with measurements taken on Oct. 10, 2008 ("Test 1"). At Blairsville, Ga., 'Tift 10' and 'Tift-17' were planted on Jun. 2, 2006 and May 27, 2007, with measurements taken on Oct. 18, 2006 and Sep. 27, 2007, respectively. At Griffin, Ga., 'Tift 10' and 'Tift-17' were planted on May 14, 2009, with measurements taken on Oct. 2, 2006.

TABLE 10

Summary of morphological characteristics of two *Pennisetum* grasses.

| Trait | 'Tift 17' | 'Tift 10' |
|---|---|---|
| Mature plant height | 72-148 cm | 108-155 cm |
| Diameter of plant canopy | 133-163 cm | 133-155 cm |
| Leaf width | 30-33 mm | 38-42 mm |
| Leaf length | 61-83 cm | 61-79 cm |
| Base diameter at ground level, individual plants | 22-48 cm | 25-49 cm |
| Number of leaves/culm | 9.6 | 11.3 |
| Leaf Angle (Culm:Leaf) | 27 degrees | 19 degrees |
| Midrib color | Greyed-purple 187D | Greyed-purple 186B |
| Inflorescence | None | Yes |
| *Helminthosporium* leaf spot on mature plants | None | None |

In summary, 'Tift 10' is similar to 'Tift-17' in canopy diameter, plant base diameter, leaf length, and disease resistance. 'Tift 10' is taller, has wider leaves, a smaller culm-leaf angle, produces more leaves per culm, and produces exserted inflorescence at daylight of approximately 10.5 h or less. 'Tift 10' has more attractive color than 'Tift-17'.

BRIEF DESCRIPTION OF THE FIGURES

The accompanying colored photographs illustrate the overall appearance and distinct characteristics of the new variety of *Pennisetum* 'Tift 10'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

FIG. 1 is a photograph of the new variety *Pennisetum* 'Tift 10'.

BOTANICAL DESCRIPTION

The new variety 'Tift 10' is a perennial at Tifton, Ga. (USDA Zone 8a). The new variety 'Tift 10' survived at approximately −7° C. for one night and 13 nights below 0° C. in the field during the 2008/2009 winter at Tifton. It has neither survived the winter temperatures (below 0° C. for 45 days and a low temperature of −10° C. during 2008/2009) in Griffin, Ga. (USDA Zone 7b) nor those (lows of −13° C. and −15° C. in 2006/2007 and 2007/2008, respectively) in the mountains of Blairsville, Ga. (USDA Zone 6b). Because of its vigor, it can effectively be used as an annual where it will not survive freezing temperatures in the winter.

All data are from plants established as single stem propagules in mid-May, and rated in September through October, except the 2007 and 2009 Test 1 data are from plants that over-wintered at Tifton. Plants were spaced at 2 meter centers.

Plant:

*Mature plant height*.—Approximately 108-155 cm.

*Diameter of plant canopy*.—Approximately 133-155 cm.

*Leaf width*.—Approximately 38-42 mm.

*Leaf length*.—Approximately 69-79 mm.

*Adaxial leaf surface trichomes*.—Sparse, 1 mm.

*Abaxial leaf surface trichomes*.—None.

*Leaf blade margin trichome length*.—<0.1 mm.

*Leaf collar trichome length*.—Dense, 4 mm.

*Leaf blade edge at collar trichome*.—Dense at base (5 mm) for 7 cm from collar.

*Sheath trichomes*.—None.

*Adaxial leaf color*.—About Greyed-purple RHS 187A.

*Abaxial leaf color*.—About Greyed-purple RHS 186A.

*Midrib color*.—About Greyed-purple RHS 186B.

*Helminthosporium leaf spot on mature plants*.—None.

*Inflorescence on Oct.* 20, 2008.—Yes.

What is claimed is:

1. A new and distinct variety of the *Pennisetum* plant named 'Tift 10', substantially as illustrated and described herein.

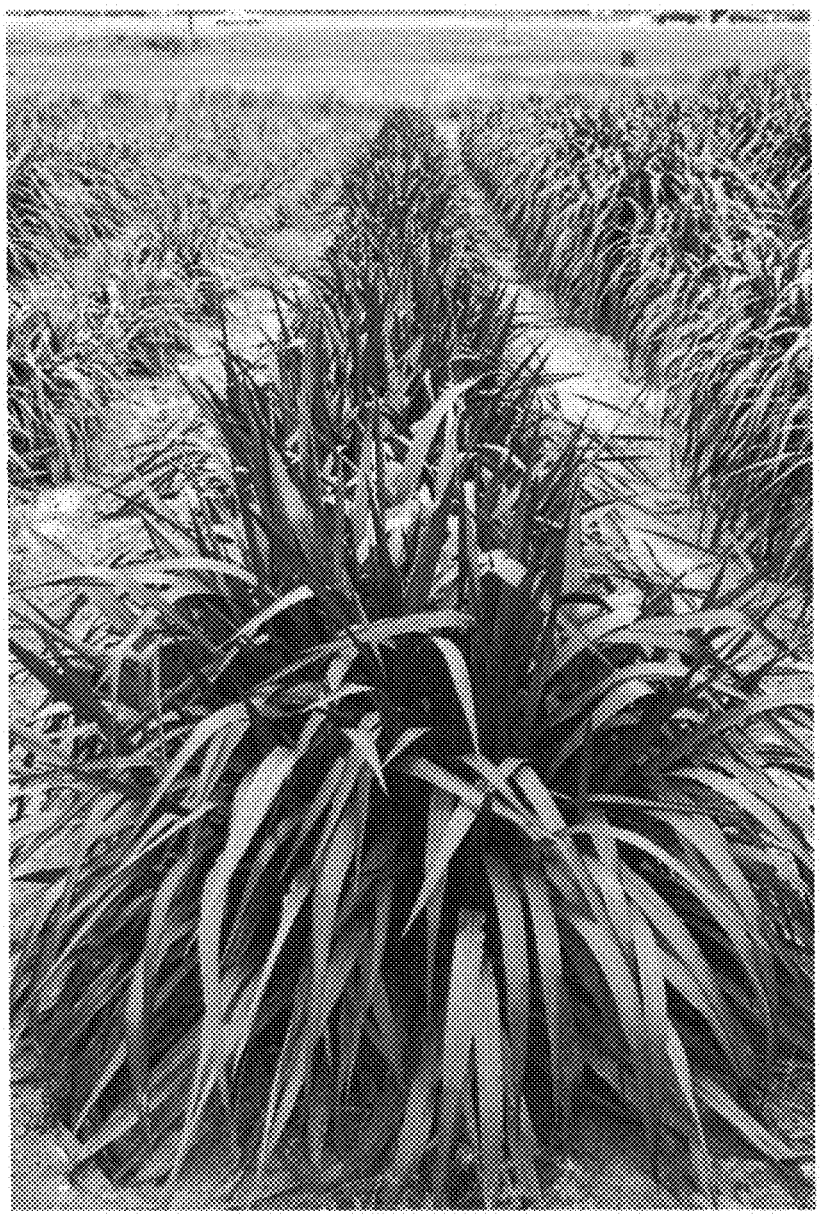

* * * * *